United States Patent [19]

Gilpin et al.

[11] Patent Number: 4,562,280

[45] Date of Patent: Dec. 31, 1985

[54] CHLOROMETHYLATION OF DEACTIVATED AROMATIC COMPOUNDS

[75] Inventors: Jo Ann Gilpin; Lowell B. Lindy, both of Midland, Mich.

[73] Assignee: The Dow Chemical Company, Midland, Mich.

[21] Appl. No.: 662,461

[22] Filed: Oct. 18, 1984

[51] Int. Cl.$^4$ ............................................. C07C 69/76
[52] U.S. Cl. ..................... 560/103; 560/20; 560/100; 560/102; 564/166; 568/936; 570/194; 585/462
[58] Field of Search ................ 560/103, 20, 100, 102; 570/194; 585/462; 564/166; 568/936

[56] References Cited

U.S. PATENT DOCUMENTS

| | | | |
|---|---|---|---|
| 1,879,912 | 9/1932 | Schmidt et al. | 585/462 |
| 1,972,956 | 9/1934 | Seymour | 585/462 |
| 2,219,873 | 10/1939 | Pinkernelle | 570/194 |
| 2,361,065 | 10/1944 | Schmerling et al. | 585/462 |
| 2,361,355 | 10/1944 | Sachanen et al. | 585/462 |
| 2,402,847 | 6/1946 | Schmerling et al. | 585/462 |
| 2,423,530 | 7/1947 | Thacker et al. | 585/462 |
| 2,436,151 | 2/1948 | O'Kelly et al. | 585/462 |
| 2,882,325 | 4/1959 | Lewisi et al. | 585/462 |
| 4,070,366 | 1/1978 | Gregorovich et al. | 585/462 |

FOREIGN PATENT DOCUMENTS 925627  5/1963  United Kingdom ................ 585/462

*Primary Examiner*—Paul J. Killos
*Attorney, Agent, or Firm*—Norman L. Sims

[57] ABSTRACT

The invention is a process for the chloromethylation of an aromatic compound, substituted with an alkyl group and a deactivating moiety, which comprises contacting an aromatic compound, substituted with an alkyl group and a deactivating group, with a chloromethyl alkyl ether in the presence of a catalytic amount of ferric chloride or stannic chloride, under conditions such that an aromatic compound, substituted with an alkyl group, a chloromethyl group, and a deactivating group, wherein the alkyl and chloromethyl groups are on adjacent carbon atoms, is prepared.

16 Claims, No Drawings

CHLOROMETHYLATION OF DEACTIVATED AROMATIC COMPOUNDS

BACKGROUND OF THE INVENTION

This invention relates to the chloromethylation of deactivated aromatic compounds, more particularly to aromatic compounds substituted with alkyl groups and deactivating substituents.

The chloromethylation of aromatic compounds is a well-known reaction. It is well-known that the result of a chloromethylation reaction depends greatly on the nature of the chloromethylating agent, the catalyst, and the process conditions. Effective chloromethylating agents are formaldehyde, paraformaldehyde or trioxymethylene with hydrogen chloride, and monochloromethyl and α,α'-bischloromethyl ethers. The reaction is carried out in the presence of zinc chloride, stannous chloride, stannic chloride, aluminum trichloride, boron trifluoride, ferric chloride, titanium tetrachloride, as well as protic acids —HCL (taken in excess and behaving simultaneously as a reactant), $H_2SO_4$, $H_3PO_4$, $ClSO_3H$ and $CH_3COOH$. Zinc chloride is used most frequently. To increase its activity, it is often used with a small amount of aluminum chloride. The chloromethylation of unsubstituted aromatics and alkyl-substituted aromatics is relatively straightforward using the above-described chloromethylation agents and catalysts.

The chloromethylation of aromatic compounds with deactivating substituents requires relatively severe reaction conditions. The chloromethylation of deactivated aromatic compounds can be performed by treatment with formaldehyde and HCl in concentrated sulfuric acid. Specific difficulties arise in the chloromethylation of alkylaryl ketones. In the absence of activating substituents in the benzene ring, the alpha position in the side chain is substituted. The reported cases of chloromethylation of aromatic carboxylic acids, and their esters, have been carried out either in concentrated sulfuric acid solutions or in the presence of substantial amounts of zinc chloride catalyst. Nitrobenzene is not easily chloromethylated. It has been found that nitrobenzene can be chloromethylated using paraformaldehyde and hydrogen chloride in concentrated sulfuric acid at 90° C. to 100° C. Nitrotoluene has been chloromethylated with nearly a quantitative yield in 24 hours using di(chloromethyl)ether with chlorosulfonic acid, or oleum, at temperatures below 10° C. By carrying out this reaction at 40° C. to 50° C. with a large excess of di(chloromethyl)ether in the presence of a larger amount of chlorosulfonic acid or 20 percent oleum, bis-chloromethylated product can be obtained.

Chloromethyl ethers such as bischloromethyl ether and monochloromethyl ether have been used to chloromethylate deactivated aromatics. Usually such deactivated compounds are acted upon by chloromethyl ethers in sulfuric acid or oleum, sometimes in the presence of chlorosulfonic acid.

As described hereinbefore, heretofore known processes for the chloromethylation of deactivated aromatic compounds require the use of relatively harsh conditions and large amounts of protic acids. Furthermore, large amounts of catalysts are normally used for these reactions. Many of the processes use the very reactive and highly toxic bischloromethyl ether. The use of highly active catalysts often results in the formation of unwanted by-products such as diarylmethane derivatives.

What is needed is a process for the chloromethylation of aromatic compounds substituted with deactivating substituents wherein addition of protic mineral acids are not required, relatively mild conditions can be used, less toxic reagents are used, and relatively low by-product formation is experienced.

SUMMARY OF THE INVENTION

The invention is a process for the chloromethylation of an aromatic compound, substituted with an alkyl group and a deactivating moiety, which comprises contacting an aromatic compound, substituted with an alkyl group and a deactivating group, with a chloromethyl alkyl ether in an inert organic reaction medium in the presence of a catalytic amount of $FeCl_3$ or $SnCl_4$, under conditions such that an aromatic compound, substituted with an alkyl group, a chloromethyl group, and a deactivating group, wherein the alkyl and chloromethyl groups are on adjacent carbon atoms, is prepared.

The process of this invention has several advantages over the known processes. The aromatic compounds substituted with alkyl and deactivated substituents are prepared under relatively mild conditions in the absence of added protic mineral acids and the highly toxic bischloromethyl ether. Furthermore, the process of this invention results in low by-product formation.

DETAILED DESCRIPTION OF THE INVENTION

Any aromatic compound which is substituted with an alkyl group and a deactivating substituent may be chloromethylated by the process of this invention. Preferred aromatic radicals include benzene, naphthalene, phenanthrene, anthracene, biaryl radicals, or two or more aromatic radicals bridged by alkylene or cycloalkylene moieties. More preferred aromatic radicals are benzene, naphthalene, biphenyl, binaphthyl, diphenylalkane or diphenylcycloalkane radicals. The most preferred aromatic radical is benzene. Deactivating substituent refers herein to any substituent which results in deactivation of an aromatic ring toward electrophilic substitution. Preferred deactivating substituents include hydrocarbyloxycarbonyl, hydrocarbylamido, hydrocarbylcarbonyl, carboxyl, carbonylhalo, nitro, sulfone or sulfoxide moieties. More preferred deactivating substituents include hydrocarbyloxycarbonyl, hydrocarbylamido and nitro moieties. Even more preferred deactivating substituents are alkyloxycarbonyl and alkylamido moieties. The most preferred class of deactivating substituents are the alkyloxycarbonyls.

Preferred aromatic compounds substituted with alkyl and deactivating groups correspond to the formula $R^1$—Ar—$R^2$ wherein $R^1$ is a $C_{1-10}$ lower alkyl group; $R^2$ is a hydrocarbyloxycarbonyl, a hydrocarbylamido, hydrocarbylcarbonyl, carboxyl, carbonylhalo, nitro, sulfone or sulfoxide group; and Ar is an aromatic radical. In that embodiment wherein Ar is benzene, preferred alkyl-deactivating moiety-substituted benzenes include those which correspond to the following formula

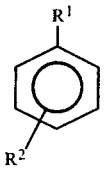

wherein R¹ and R² are as hereinbefore defined.

The product of this invention is an aromatic compound substituted with an alkyl group, a chloromethyl group, and a deactivating substituent, wherein the alkyl group and chloromethyl group are on adjacent carbon atoms of one of the aromatic rings. The preferred products of this invention correspond to the formula

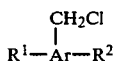

wherein R¹ and R² are as hereinbefore defined. In that embodiment wherein Ar is benzene, a preferred deactivating group substituted-alkyl-chloromethyl-benzene corresponds to the formula

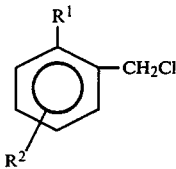

wherein R¹ and R² are as hereinbefore defined.

Preferred compounds prepared by the process of this invention include methyl 3-chloromethyl-4-methylbenzoate, methyl 3-chloromethyl-4-ethylbenzoate, methyl 3-chloromethyl-4-propylbenzoate, methyl 3-chloromethyl-4-butylbenzoate, ethyl 3-chloromethyl-4-methylbenzoate, ethyl 3-chloromethyl-4-ethylbenzoate, ethyl 3-chloromethyl-4-propylbenzoate, ethyl 3-chloromethyl-4-butylbenzoate, propyl 3-chloromethyl-4-methylbenzoate, propyl 3-chloromethyl-4-ethylbenzoate, propyl 3-chloromethyl-4-propylbenzoate, propyl 3-chloromethyl-4-butylbenzoate, butyl 3-chloromethyl-4-methylbenzoate, butyl 3-chloromethyl-4-ethylbenzoate, butyl 3-chloromethyl-4-propylbenzoate, butyl 3-chloromethyl-4-butylbenzoate, 1-methyl-2-chloromethyl-4-nitrobenzene, 1-ethyl-2-chloromethyl-4-nitrobenzene, 1-propyl-2-chloromethyl-4-nitrobenzene, 1-butyl-2-chloromethyl-4-nitrobenzene, N-methyl-3-chloromethyl-4-methylbenzamide, N-methyl-3-chloromethyl-4-ethylbenzamide, N-methyl-3-chloromethyl-4-propylbenzamide, N-methyl-3-chloromethyl-4-butylbenzamide, N-ethyl-3-chloromethyl-4-methylbenzamide, N-ethyl-3-chloromethyl-4-ethylbenzamide, N-ethyl-3-chloromethyl-4-propylbenzamide, N-ethyl-3-chloromethyl-4-butylbenzamide, N-propyl-3-chloromethyl-4-methylbenzamide, N-propyl-3-chloromethyl-4-ethylbenzamide, N-propyl-3-chloromethyl-4-propylbenzamide, N-propyl-3-chloromethyl-4-butylbenzamide, N-butyl-3-chloromethyl-4-methylbenzamide, N-butyl-3-chloromethyl-4-ethylbenzamide, N-butyl-3-chloromethyl-4-propylbenzamide and N-butyl-3-chloromethyl-4-butylbenzamide. More preferred compounds prepared by the process of this invention include methyl 3-chloromethyl-4-methylbenzoate, methyl 3-chloromethyl-4-ethylbenzoate, methyl 3-chloromethyl-4-propylbenzoate, methyl 3-chloromethyl-4-butylbenzoate, ethyl 3-chloromethyl-4-methylbenzoate, ethyl 3-chloromethyl-4-ethylbenzoate, ethyl 3-chloromethyl-4-propylbenzoate, ethyl 3-chloromethyl-4-butylbenzoate, propyl 3-chloromethyl-4-methylbenzoate, propyl 3-chloromethyl-4-ethylbenzoate, propyl 3-chloromethyl-4-propylbenzoate, propyl 3-chloromethyl-4-butylbenzoate, butyl 3-chloromethyl-4-methylbenzoate, butyl 3-chloromethyl-4-ethylbenzoate, butyl 3-chloromethyl-4-propylbenzoate and butyl 3-chloromethyl-4-butylbenzoate, with methyl 3-chloromethyl-4-methylbenzoate being most preferred.

Preferred starting compounds are methyl 4-methylbenzoate, methyl 4-ethylbenzoate, methyl 4-propylbenzoate, methyl 4-butylbenzoate, ethyl 4-methylbenzoate, ethyl 4-ethylbenzoate, ethyl 4-propylbenzoate, ethyl 4-butylbenzoate, propyl 4-methylbenzoate, propyl 4-ethylbenzoate, propyl 4-propylbenzoate, propyl 4-butylbenzoate, butyl 4-methylbenzoate, butyl 4-ethylbenzoate, butyl 4-propylbenzoate, butyl 4-butylbenzoate, 1-methyl-4-nitrobenzene, 1-ethyl-4-nitrobenzene, 1-propyl-4-nitrobenzene, 1-butyl-4-nitrobenzene, N-methyl-4-methylbenzamide, N-methyl-4-ethylbenzamide, N-methyl-4-propylbenzamide, N-methyl-4-butylbenzamide, N-ethyl-4-methylbenzamide, N-ethyl-4-ethylbenzamide, N-ethyl-4-propylbenzamide, N-ethyl-4-butylbenzamide, N-propyl-4-methylbenzamide, N-propyl-4-ethylbenzamide, N-propyl-4-propylbenzamide, N-propyl-4-butylbenzamide, N-butyl-4-methylbenzamide, N-butyl-4-ethylbenzamide, N-butyl-4-propylbenzamide and N-butyl-4-butylbenzamide. More preferred starting compounds of this invention include methyl 4-methylbenzoate, methyl 4-ethylbenzoate, methyl 4-propylbenzoate, methyl 4-butylbenzoate, ethyl 4-methylbenzoate, ethyl 4-ethylbenzoate, ethyl 4-propylbenzoate, ethyl 4-butylbenzoate, propyl 4-methylbenzoate, propyl 4-ethylbenzoate, propyl 4-propylbenzoate, propyl 4-butylbenzoate, butyl 4-methylbenzoate, butyl 4-ethylbenzoate, butyl 4-propylbenzoate and butyl 4-butylbenzoate, with methyl 4-methylbenzoate being most preferred.

In the process of this invention an aromatic compound substituted with an alkyl group and a deactivating group is chloremethylated with an alkyl chloromethyl ether optionally in the presence of an inert organic reaction medium in the presence of a catalytic amount of ferric chloride or stannic chloride, and optionally in the presence of a reaction promoter.

The chloromethylating agent useful in this invention is any chloromethyl alkyl ether. Preferred chloromethyl alkyl ethers correspond to the formula $ClCH_2OR^3$ wherein $R^3$ is $C_{1-10}$ alkyl or $C_{3-10}$ haloalkyl. Examples of chloromethyl alkyl ethers useful in this invention include chloromethyl methyl ether, chloromethyl ethyl ether, chloromethyl propyl ether, chloromethyl butyl ether, and 1-chloromethoxy-4-chlorobutane. A most preferred chloromethyl alkyl ether is chloromethyl methyl ether.

Catalysts useful in this invention are ferric chloride ($FeCl_3$) and stannic chloride ($SnCl_4$). The catalysts may be used in amounts which are catalytic for the chloromethylation of the aromatic compounds containing alkyl and deactivating substituents. Preferably, about 2 percent or greater, based upon the weight of the aromatic compound, may be used. More preferably, between about 4 and 100 weight percent may be used. Even more preferably, between about 5 and 60 weight percent may be used with between about 15 an 40 weight percent being most preferred.

Reaction promoter refers herein to compounds which increase the yield and rate of reaction when present. Preferred reaction promoters include thionyl chloride (SOCl$_2$), silicon tetrachloride (SiCl$_4$), titanium tetrachloride (TiCl$_4$), phosphorus trichloride (PCl$_3$), sulfuryl chloride (SO$_2$Cl$_2$), phosphorus pentachloride (PCl$_5$) and chlorosulfonic acid (ClSO$_3$H). More preferred reaction promoters include thionyl chloride, silicon tetrachloride, titanium tetrachloride, phosphorus trichloride and sulfuryl chloride. Even more preferred reaction promoters include thionyl chloride and phosphorus trichloride, with thionyl chloride being the most preferred. The reaction promoter is an optional ingredient, and may be used in amounts which result in enhanced yields of the desired product and rates. Preferably, about 10 mole percent or greater based upon the aromatic compound may be used. The upper limit on the amount of promoter used is dictated by economics. More preferably, between about 10 and 100 mole percent of the promoter may be used, based on the aromatic compound. Even more preferably, between about 10 and 80 mole percent of the promoter may be used, with between about 20 and 40 mole percent being most preferred.

In those embodiments where no reaction promoter may be used, a larger amount of catalyst may be required to get the desired result.

The amount of chloromethylating agent which may be used is that amount which results in the desired yield of the chloromethylated aromatic product. Preferably, a mole ratio of 2:1 or greater of the chloromethylating agent is used. Preferably, the mole ratio of chloromethylating agent to aromatic compound is between about 2:1 and 6:1, and most preferably between about 2:1 and 4:1. Above a mole ratio of 6:1, the reaction becomes uneconomical, whereas below a mole ratio of 2:1, the reaction proceeds very slowly, and may not go to completion.

This process may be performed in an inert reaction medium. Alternatively, the process may be performed in an excess of the chloromethylating agent. Preferable inert reaction media include carbon disulfide, chlorinated aliphatic hydrocarbons and aliphatic hydrocarbons. Preferred inert reaction media include methylene chloride, carbon tetrachloride, chloroform, perchloroethylene, 1,2-dichloroethane, ligroin or carbon disulfide.

This process may be performed at temperatures wherein the desired reaction takes place. Preferred temperatures are between about 40° C. and 80° C., with between about 40° C. and 60° C. being more preferred, and between about 50° C. and 60° C. being most preferred.

The aromatic compound substituted with alkyl, chloromethyl and deactivating substituents can be recovered by contacting the reaction media with a quenching agent such as an alcohol or water so as to inactivate chlomethylating agents and catalysts, thereafter stripping off the volatiles, and then washing the resultant mixture with water to remove the catalyst. Thereafter the product can be recovered by distillation or recrystallization.

This process may be performed at atmospheric and superatmospheric pressures.

In the hereinbefore presented formulas, Ar is preferably benzene, naphthalene, phenanthrene, anthracene, a biaryl moiety, or two or more aromatic radicals bridged by an alkylene or cycloalkylene moiety. Ar is more preferably benzene, naphthalene, biphenyl, binaphthyl, diphenylalkane or diphenylcycloalkane radicals. Ar is most preferably benzene. $R^1$ is preferably C$_{1-4}$ alkyl and most preferably methyl. $R^2$ is preferably hydrocarbyloxycarbonyl, hydrocarbylamido, or nitro. $R^2$ is more preferably alkoxycarbonyl or alkylamido. $R^2$ is even more preferably alkoxycarbonyl. $R^2$ is most preferably methoxycarbonyl. $R^3$ is preferably C$_{1-4}$ alkyl and most preferably methyl.

Hydrocarbyl means herein an organic radical containing carbon and hydrogen atoms. The term hydrocarbyl includes the following organic radicals: alkyl, cycloalkyl, aryl, aliphatic and cycloaliphatic aralkyl and alkaryl. Aliphatic refers herein to straight- and branched-, and saturated hydrocarbon chains, that is, alkyl. Cycloaliphatic refers herein to saturated hydrocarbons, that is, cycloalkyl. The term aryl refers herein to biaryl, biphenylyl, phenyl, naphthyl, phenanthranyl, anthranyl and two aryl groups bridged by an alkylene group. Alkaryl refers herein to an alkyl-substituted aryl substituent wherein aryl is as defined hereinbefore. Aralkyl means herein an alkyl group substituted with an aryl group, wherein aryl is as defined hereinbefore. C$_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. C$_{1-5}$ alkyl incudes methyl, ethyl, propyl, butyl and pentyl.

Cycloalkyl refers to alkyl groups containing one, two three or more cyclic rings.

Hydrocarbylcarbonyl refers herein to a substituent which is a hydrocarbyl moiety bonded to a carbonyl moiety (commonly known as a ketone moiety) and includes substituents which correspond to the formula

wherein $R^4$ is C$_{1-10}$ alkyl.

Hydrocarbyloxycarbonyl refers herein to a substituent in which a hydrocarbyl moiety is bonded to an oxygen atom which is further bonded to a carbonyl moiety (commonly referred to as an ester moiety) and includes substituents which correspond to the formula

wherein $R^4$ is C$_{1-10}$ alkyl.

Hydrocarbylamido refers herein to a substituent in which a hydrocarbyl moiety is bonded to an amide group and corresponds to the formula

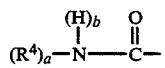

wherein $R^4$ is C$_{1-10}$ alkyl, a is 1 or 2 and b is 0 or 1.

In one more preferred embodiment, this invention is a process for the chloromethylation of an alkyl alkylbenzoate wherein the alkyl alkylbenzoate is contacted with chloromethylmethyl ether in a chlorinated hydrocarbon or carbon disulfide reaction medium in the presence of a catalytic amount of ferric chloride and a reaction promoter comprising thionyl chloride under conditions such that an alkyl 1-alkyl-2-chloromethylbenzoate is prepared. This process can best be illustrated by the following equation

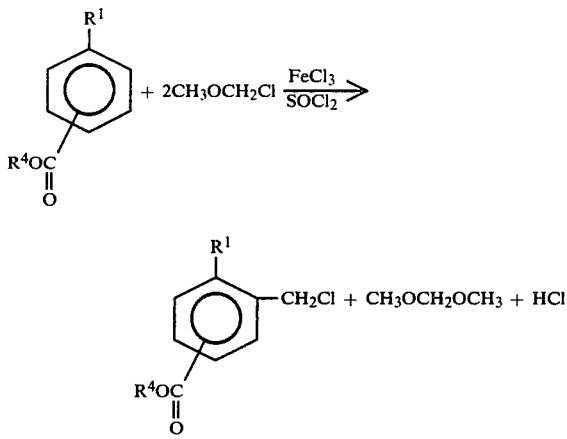

wherein $R^4$ is $C_{1-10}$ alkyl and $R^1$ is as hereinbefore defined.

The process of this invention wherein the catalyst and reaction promoter is used results in yields of the desired product of 30 or greater, more preferably 50 or greater. The process of this invention wherein ferric chloride and thionyl chloride are used as the catalyst and reaction promoter, respectively, result in a yield of the desired product of 40 or greater, preferably 65 or greater.

SPECIFIC EMBODIMENTS

The following examples are included for illustrative purposes only, and do not limit the scope of the invention or claims. Unless otherwise stated, all parts and percentages are by weight.

EXAMPLE 1

Chloromethylation of methyl para-toluate using chloromethylmethyl ether, ferric chloride catalyst and thionyl chloride A solution of methyl para-toluate (30 g, 0.20 mole) in 1,2-dichloroethane (80 ml) is added to a flask equipped with ice bath, stirrer, water-cooled condenser, ice traps and scrubber. To the stirred solution is added chloromethylmethyl ether (48 ml, 0.63 mole), thionyl chloride (5.8 ml, 0.080 mole), and last ferric chloride (6.5 g, 0.040 mole) in two portions. The cooling bath is removed, and the stirred reaction mixture is heated at 60° C. for 3 hours.

Methanol (150 ml) is added gradually to the cooled reaction mixture. Low boiling components are removed under vacuum. The solution of product in dichloroethane is washed with water, 5 percent sodium bicarbonate solution, dried over anhydrous magnesium sulfate, filtered, and solvent is removed under vacuum. The product contains 13 percent unreacted methyl para-toluate and 80 percent methyl 3-chloromethyl-4-methylbenzoate as analyzed by capillary gas chromatography. Recovery of the starting material by vacuum distillation affords a distillation residue of 91 percent pure product (analysis by capillary gas chromatography).

EXAMPLE 2

Chloromethylation of methyl para-toluate using chloromethylmethyl ether and ferric chloride catalyst The chloromethylation is conducted as described in Example 1 with methyl para-toluate (30 g, 0.20 mole) in 1,2-dichloroethane (85 ml), chloromethylmethyl ether (51 ml, 0.67 mole) and ferric chloride (6.5 g, 0.040 mole) at 60° C. for 4 hours.

The reaction product contains 58 percent unreacted methyl para-toluate and 42 percent methyl 3-chloromethyl-4-methylbenzoate. Distillation of unreacted starting material affords a distillation residue of 97 percent pure methyl 3-chloromethyl-4-methylbenzoate (analysis by capillary gas chromatography).

EXAMPLES 3-4

Examples 3 and 4 are run in accordance with the procedure of Example 1. The conditions and results are compiled in Table I along with the conditions and results of Examples 1 and 2.

TABLE I

| Example | Mole Ratio/ 1.0 mole Methyl p-Toluate | | | Conversion to Product | | | Isolated Product CMMT[2,3] |
|---|---|---|---|---|---|---|---|
| | CMME[1] | FeCl₃ Catalyst | Thionyl Chloride | Time (hr) @ 60° C. | Normalized Area % (GC) | | |
| | | | | | Methyl p-Toluate | CMMT[2] | |
| 1 | 3.1 | 0.20 | 0.40 | 0.5 | 42 | 58 | — |
| | | | | 1.0 | 28 | 72 | — |
| | | | | 2.0 | 19 | 81 | — |
| | | | | 3.0 | 14 | 86 | 91 |
| 2 | 3.3 | 0.20 | — | 0.5 | 78 | 22 | — |
| | | | | 1.0 | 71 | 29 | — |
| | | | | 2.0 | 65 | 35 | — |
| | | | | 3.0 | 61 | 39 | — |
| | | | | 4.0 | 58 | 42 | 97 |
| 3 | 6.2 | 0.40 | — | 0.5 | 55 | 45 | — |
| | | | | 1.0 | 42 | 58 | — |
| | | | | 2.0 | 30 | 70 | — |
| | | | | 3.0 | 22 | 78 | — |
| | | | | 4.0 | 18 | 82 | 91 |
| 4 | 6.2 | 0.40 | 0.20 | 0.5 | 16 | 84 | — |
| | | | | 1.0 | 8 | 92 | — |
| | | | | 2.0 | 3 | 97 | — |

TABLE I-continued

| | Mole Ratio/ 1.0 mole Methyl p-Toluate | | Conversion to Product | | | Isolated |
|---|---|---|---|---|---|---|
| | | | Time | Normalized Area % (GC) | | Product |
| Example | CMME[1] | FeCl₃ Catalyst | Thionyl Chloride | (hr) @ 60° C. | Methyl p-Toluate | CMMT[2] | CMMT[2,3] |
| | | | | 3.0 | 1 | 99 | 83 |

[1]Chloromethyl methyl ether
[2]Methyl 3-chloromethyl-4-methylbenzoate
[3]Product purity by capillary gas chromatography - area %

What is claimed is:

1. A process for the chloromethylation of an aromatic compound, substituted with an alkyl group and a deactivating moiety, which comprises contacting an aromatic compound, substituted with an alkyl group and a deactivating group, with a chloromethyl alkyl ether in the presence of a catalytic amount of ferric chloride or stannic chloride, under conditions such that an aromatic compound, substituted with an alkyl group, a chloromethyl group, and a deactivating group, wherein the alkyl and chloromethyl groups are on adjacent carbon atoms, is prepared.

2. The process of claim 1 wherein the contacting occurs in an inert organic reaction media.

3. The process of claim 2 wherein the contacting occurs in the presence of a reaction promoter comprising $SOCl_2$, $SiCl_4$, $TiCl_4$, $PCl_3$, $SO_2Cl_2$, $PCl_5$ or $ClSO_3H$.

4. The process of claim 3 wherein the aromatic compound substituted with an alkyl group and a deactivating group corresponds to the formula

the aromatic compound substituted with an alkyl group, chloromethyl group and a deactivating group, wherein the alkyl and chloromethyl groups are on adjacent carbon atoms corresponds to the formula

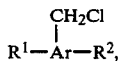

and the chloromethylalkyl ether corresponds to the formula

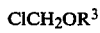

wherein
Ar is an aromatic radical;
$R^1$ is a $C_{1-10}$ lower alkyl group;
$R^2$ is a hydrocarbyloxycarbonyl, a hydrocarbylamido, hydrocarbylcarbonyl, carboxyl, carbonylhalo, nitro, sulfone or sulfoxide; and
$R^3$ is $C_{1-10}$ alkyl or $C_{3-10}$ haloalkyl.

5. The process of claim 4 wherein at least about 2 percent by weight based on the aromatic compound of the catalyst, and at least about 10 percent by weight based on the aromatic compound of the promoter are present.

6. The process of claim 5 wherein the catalyst is present in an amount of between about 5 and 60 percent by weight of the aromatic compound, and the promoter is present in an amount of between about 10 and 80 percent by weight based on the aromatic compound.

7. The process of claim 6 wherein the promoter is $SOCl_2$, $SiCl_4$, $TiCl_4$, $PCl_3$ or $SO_2Cl_2$.

8. The process of claim 7 wherein the promoter is $SOCl_2$.

9. The process of claim 8 wherein the catalyst is $FeCl_3$.

10. The process of claim 9 wherein
Ar is a benzene, naphthalene, phenanthrene, anthracene, a biaryl moiety, or two or more aromatic radicals bridged by alkylene or cycloalkylene moieties;
$R^1$ is $C_{1-4}$ alkyl;
$R^2$ is hydrocarbyloxycarbonyl, hydrocarbylamido or nitro; and
$R^3$ is $C_{1-4}$ alkyl.

11. The process of claim 10 wherein
Ar is benzene, naphthalene, biphenyl, binaphthyl, diphenylalkane or diphenyl cycloalkane radical; and
$R^2$ is alkoxy carbonyl or alkylamido.

12. The process of claim 11 wherein
Ar is benzene;
$R^1$ is methyl;
$R^2$ is alkoxy carbonyl; and
$R^3$ is methyhl.

13. The process of claim 11 wherein the inert reaction media is carbon disulfide, aliphatic hydrocarbon or a chlorinated aliphatic hydrocarbon.

14. The process of claim 13 wherein the temperature is between about 40° C. and 80° C.

15. A process for the chloromethylation of an alkyl alkylbenzoate wherein the alkyl alkylbenzoate is contacted with chloromethyl methyl ether in a chlorinated hydrocarbon or carbon disulfide reaction medium in the presence of a catalytic amount of $FeCl_3$ and a reaction promoter comprising $SOCl_2$ under conditions such that an alkyl 1-alkyl-2-chloromethylbenzoate is prepared.

16. The process of claim 14 wherein the alkyl alkylbenzoate corresponds to the formula

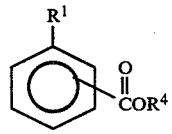

and the alkyl 1-alkyl-2-chloromethylbenzoate corresponds to the formula

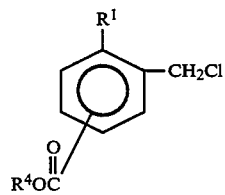

wherein $R^1$ and $R^4$ are $C_{1-10}$ alkyl.

* * * * *